United States Patent [19]
Feathers et al.

[11] Patent Number: 5,164,161
[45] Date of Patent: Nov. 17, 1992

[54] PROPORTIONAL TEMPERATURE CONTROL OF A STERILIZER

[75] Inventors: Charles H. Feathers, Hilton; Charles E. Ellis, Phelps, both of N.Y.

[73] Assignee: MDT Corporation, Torrance, Calif.

[21] Appl. No.: 649,017

[22] Filed: Feb. 1, 1991

[51] Int. Cl.⁵ .......................................... G05D 23/00
[52] U.S. Cl. ....................................... 422/109; 422/26; 422/28; 422/307; 436/55; 219/395; 219/401; 219/406; 219/413
[58] Field of Search ................... 422/109, 307, 26, 28; 436/55; 219/395, 397, 401, 406, 413

[56] References Cited

U.S. PATENT DOCUMENTS

| | | | |
|---|---|---|---|
| 3,278,256 | 10/1966 | Skaller | 422/105 |
| 4,309,381 | 1/1982 | Chamberlain et al. | 422/26 X |
| 4,447,399 | 5/1984 | Runnells et al. | 422/109 X |
| 4,865,814 | 9/1989 | Childress | 422/109 X |

Primary Examiner—Lynn M. Kummert
Attorney, Agent, or Firm—Trask, Britt & Rossa

[57] ABSTRACT

Apparatus and methods for proportional control of heating of a sterilizer chamber are disclosed in the application. A sterilizer chamber has heaters mounted on the walls, a wall temperature sensor and a chamber temperature sensor. The controller is operable to adjust the heat input by turning on the heaters for a variable fraction of a selected fixed interval and off for the remainder of the interval. When on the heaters provide a substantially constant heat input per unit time. The fraction of the interval during which the heaters are on is proportional to a temperature differential which comprises a setpoint temperature minus a temperature reading from one of the sensors. The controller has two, or in an alternate embodiment three, operating modes each having a unique temperature differential.

16 Claims, 5 Drawing Sheets

PROPORTIONAL TEMPERATURE CONTROL OF A STERILIZER

BACKGROUND OF THE INVENTION

1. Field

The invention relates generally to the art of sterilization and more particularly to the control of temperature in sterilizer chambers.

2. State of the Art

Apparatus for sterilization is used in medical, dental and other institutional settings. Both steam sterilization and chemical sterilization procedures have been developed. Accurate temperature control is needed for both types of sterilization procedures.

In typical prior art sterilizers, the heat source is controlled in a digital fashion in response to the chamber temperature. The heat source is either on, in which case heat is generated to the chamber at a constant rate, or off. When the chamber temperature falls below the desired temperature, the heat source is turned on, and when the chamber temperature exceeds the desired temperature, the heat source is turned off. This type of on/off control is very simple. However, the inherent lags in heat transfer cause considerable oscillation of the actual chamber temperature around the set temperature when such on/off control is used.

An alternate type of temperature control device varies the rate of heat transfer in response to the sensed temperature. When electric heaters are relied upon as the heat source, the input voltage to the heaters may be varied to in turn vary their heat outputs. Where the heat source is steam injected from a steam source, the flow rate of steam can be varied. However, devices employing variable heat transfer require more sophisticated hardware, and are substantially more complicated and expensive than on/off control systems.

The placement of temperature sensors also affects the performance of a heat control system. During a steam cycle, the chamber is filled with saturated steam and the temperature is uniform throughout the chamber. Thus, a sensor anywhere in the chamber will provide an accurate reading for purposes of temperature control. However, while the chamber is being warmed up prior to a cycle, or during a chemical cycle, the chamber vapor is not saturated and the temperature can vary in different parts of the chamber. In the latter case, a single sensor within the chamber will not provide accurate information for temperature control.

Thus, a need remains for sterilization apparatus having simple and inexpensive control of heating which provides accurate temperature control with a minimum of temperature oscillation. There further remains a need for such apparatus which is capable of precise temperature control for both steam and chemical cycles.

SUMMARY OF THE INVENTION

Apparatus and methods for proportional heat control system of heating of a sterilizing chamber are provided by the invention. A sterilizing chamber of this invention includes a heat source associated with the walls, a first (chamber) temperature sensor disposed within the chamber for sensing the chamber temperature, and a second (wall) temperature sensor disposed for sensing the temperature of the walls. The heat source is operable to supply heat at a constant rate to the walls.

Sterilizer control means is connected to the wall and chamber temperature sensors and to the heating means for achieving and maintaining a desired setpoint temperature in the chamber. The control means is operable to adjust the heat input to be proportional to a temperature differential which comprises the difference between a setpoint temperature and the temperature sensed by one of the sensors. Adjustment of the heat input is accomplished by turning on the heaters for a variable fraction of a selected fixed interval. The control means determines the fraction of each interval during which the heat source is turned on to achieve the necessary heat input.

The control means is further operable to apply any of several temperature differentials, singly or in combination, depending on the operating mode. The operating modes include steam sterilization cycles, chemical vapor and gas sterilization cycles, and a warm-up phase which may be executed prior to either a steam or chemical cycle. For steam cycles, a chamber temperature differential comprises the chamber setpoint temperature minus the temperature sensed by the chamber sensor. For a warm-up phase, a wall temperature differential comprises the wall setpoint minus the temperature sensed by the wall sensor.

For chemical vapor or gas cycles, in one embodiment the wall temperature differential is applied by the control means. In a preferred embodiment, a wall-chamber differential comprising the sensed wall temperature minus the sensed chamber temperature is added to the wall temperature differential to produce a combined chemical cycle differential.

BRIEF DESCRIPTION OF THE DRAWINGS

In the drawings, which illustrate what is presently regarded as the best mode for carrying out the invention.

DETAILED DESCRIPTION OF THE ILLUSTRATED EMBODIMENT

Figure 1:
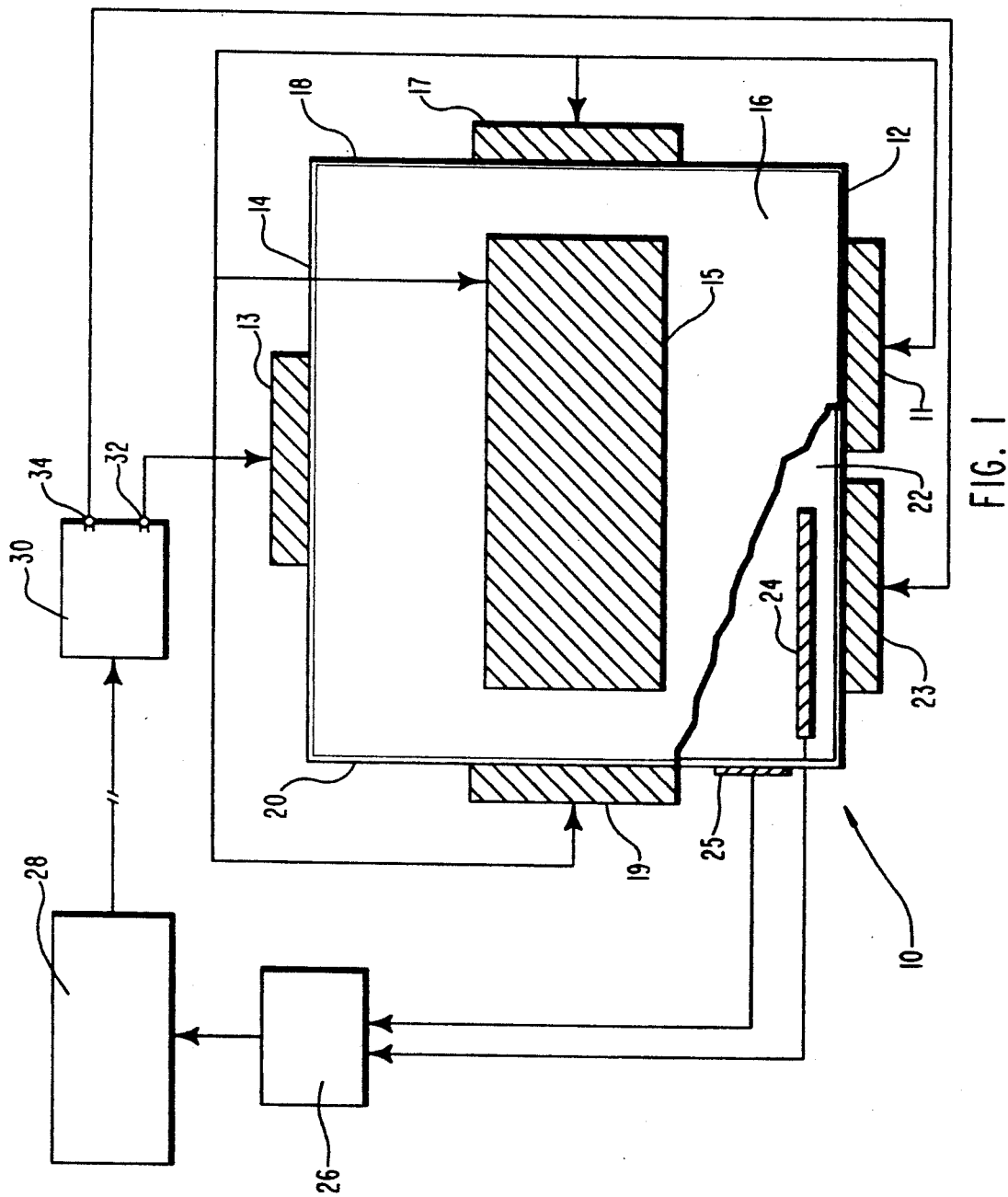
FIG. 1 is a block diagram of the invention embodied in association with an electrically heated single-walled sterilizer chamber.

In FIG. 1, a single-walled sterilizer chamber indicated generally at 10 has electric heaters 11, 13, 15, 17, 19 adapted to the exterior walls which constitute the bottom 12, top 14, back 16, and sides 18, 20 of the chamber, respectively. A heater 21 (not seen) is also associated with the chamber door 22 which forms the sixth wall (seen only in through the cutaway). Heaters 11, 13, 15, 17, 19, 21 provide heat input to the walls in a digital, on-off manner depending on whether the current to them is on or off. When current flows to the heaters, heat is generated at a constant rate, and when no current flows, no heat input is supplied.

Wall 16 of chamber 10 is shown in partially cutaway to reveal a chamber temperature sensor 24 disposed for sensing the temperature within the chamber. A wall temperature sensor 25 is disposed on wall 20 of chamber 10 for sensing the wall temperature. Preferably, sensors 24, 25 are of the kind known as resistant thermal device or RTD sensors. Platinum RTD sensors are preferred for their accuracy. However, other devices, such as thermocouples, can be used as sensors 24, 25.

The outputs from sensors 24, 25 are connected through leads to an analog-to-digital converter 26 which converts the sensor outputs to signals readable by sterilizer control means 28. Control means 28 is a microprocessor-based central processing unit of the kind widely used to control the temperature and pressure conditions within sterilizer chambers.

Control means 28 is connected to provide heat control signals to heat output means 30, which functions to supply current to heaters 11, 13, 15, 17, 19, 21. Heat output means 30 as conventionally known includes a port expander connected to a buffer or driver, which is in turn connected to a solid state relay 32. The relays function to connect an appropriate power source (not shown) to heaters 11, 13, 15, 17, 19, and 21.

In a preferred embodiment, an additional heater 23 is disposed on a portion of the chamber where extra heating is desirable, for example where the mass of metal to be heated is greater. In the illustrated embodiment, heater 23 is adapted to the bottom 12 of chamber 10. Control means 28 is further operable to independently control the heat input to different heat zones. Heat zones may be defined to include one or more heaters as desired. Heat output means 30 includes a separate relay for each zone, which is connected to the heater(s) comprising that zone. In the preferred embodiment, a first heat zone comprises heaters 11, 13, 15, 17, 19, and 21. A second heat zone comprises heater 23 on the bottom of the chamber. Control means 28 supplies separate heat signals to heat output means 30, and heat output means includes at least a second relay 34 connected to send current to heater 23.

In a practical embodiment, each of heaters 11, 13, 15, 17, 19, 21, and 23 may comprise two or more separate heating elements of equal wattage. The separate elements constituting one heater are controlled identically. Heaters 11, 13, 15, 17, 19, 21, and 23 need not be of the same wattage. The total wattage of an individual heater desirably corresponds in part to the mass of metal of the wall which is being heated.

Control means 28 adjusts the heat input to the chamber according to operating cycles of current flow to heaters 11, 13, 15, 17, 19, 21, 23. The cycles have a selected fixed time period, and control means 28 varies the fraction of the cycle during which current is sent to the heater. Control means 28 is operable to adjust the fractional "on" time of the heaters (and thereby the heat input) to be proportional to the difference between a setpoint temperature and the actual temperature sensed by one of sensors 24, 25. This difference is referred to herein as a temperature differential D. When the actual temperature is much lower than the setpoint temperature, current is supplied for a larger fraction of the operating cycle than if the actual temperature is only slightly lower than the setpoint. If the actual temperature is higher than the setpoint, then the heaters are on for little or none of the cycle.

Control means 28 is further operable to apply different temperature differentials to derive the "on" time, depending on which operating mode the sterilizer is in. The operating modes of the sterilizer may include steam sterilization, chemical vapor or gas sterilization, and warming-up. The warming-up mode is a preparatory stage which may be performed prior to either type of sterilization cycle. During steam sterilization, the steam in the chamber is saturated and therefore the temperature is exactly the same throughout the chamber. Thus, the chamber temperature differential $D_c$ (the chamber setpoint minus the actual chamber temperature) is very advantageous for determining the heat input needed to maintain the chamber temperature. However, during a warm-up phase the chamber door may be open, thus the chamber sensor reading is not useful. During a chemical cycle, the vapor or gas is not saturated and thus the temperature differs in different places in the chamber. The temperature sensed by chamber sensor 24 may be inaccurate with respect to the chamber as a whole. Therefore, for both a warm-up phase and for chemical cycles, it is preferable to use a wall temperature differential which is the wall setpoint minus the wall sensor reading to regulate the heat input.

Figure 2:
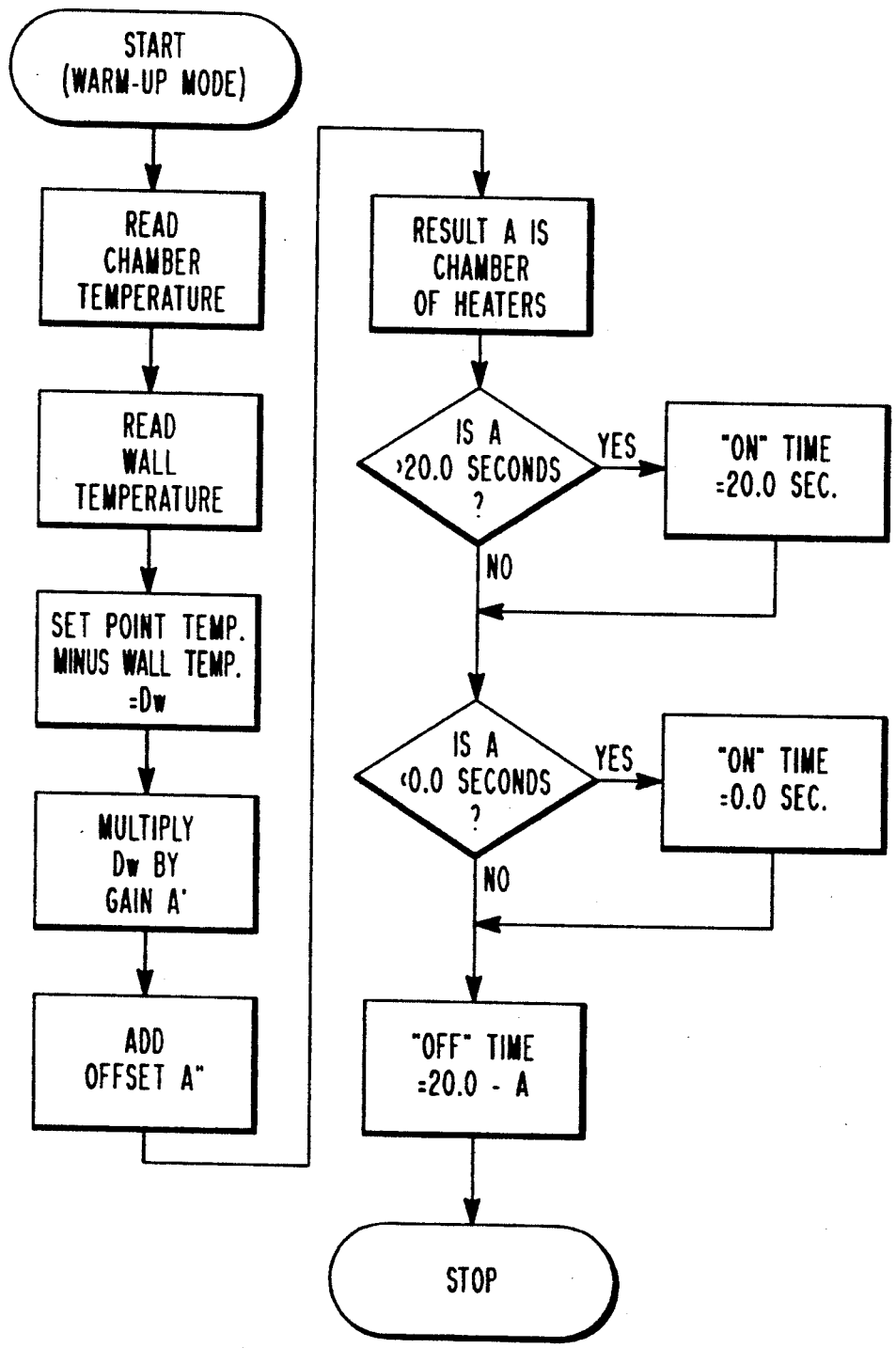
FIG. 2 is a logic flow diagram of the control means of the invention pertaining to a warm-up mode.
Figure 3:
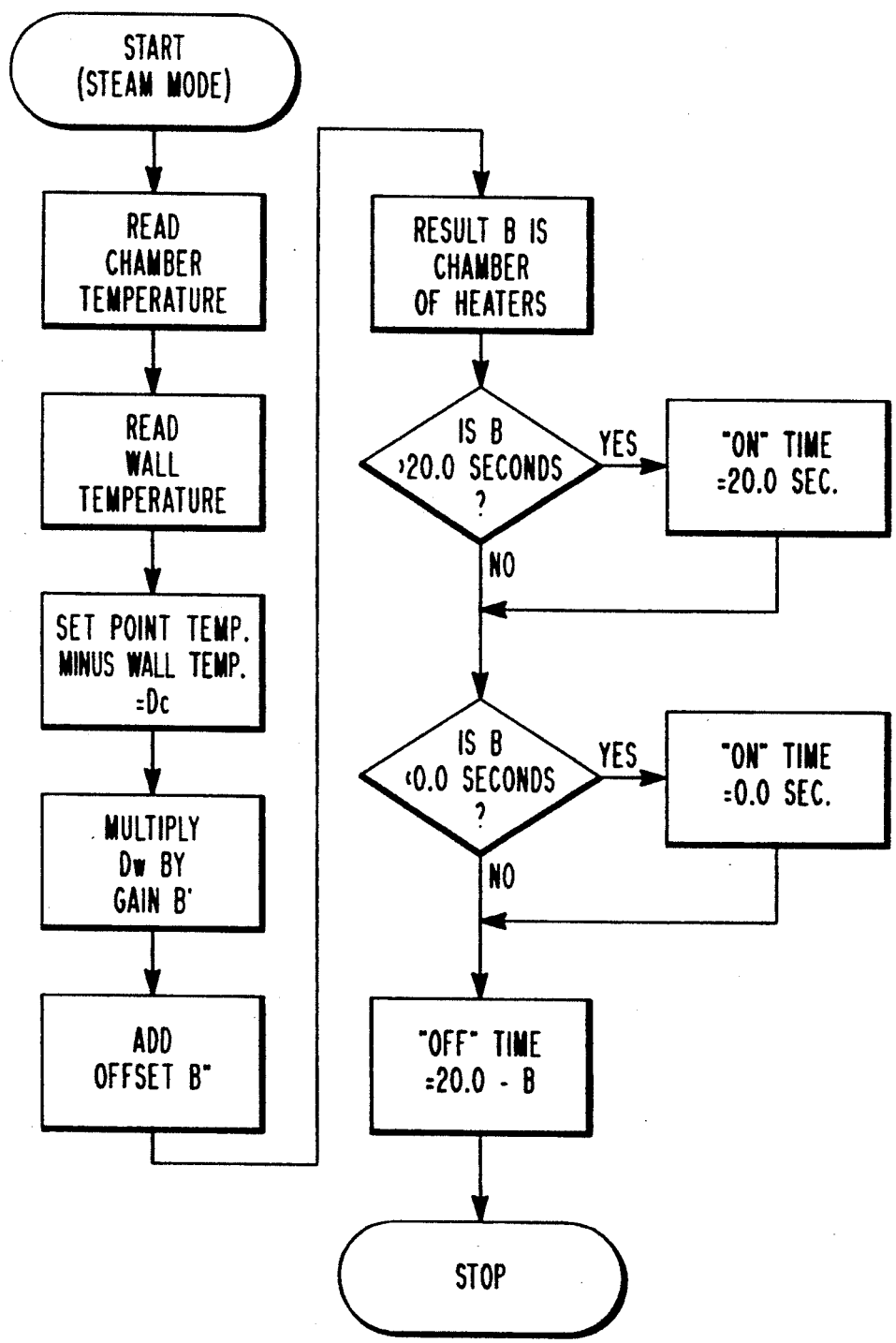
FIG. 3 is a logic flow diagram of a control means of the invention pertaining to a steam sterilization mode.

FIGS. 2 and 3 are logic flow diagrams of the operation of control means 28 in determining the operating cycles. The general features of the process will be outlined with reference to FIG. 3 which is directed to a steam sterilization mode. The control means reads the chamber temperature and subtracts it from the chamber setpoint for a steam cycle to produce the chamber temperature differential $D_c$. Temperature differential $D_c$ is then multiplied by gain factor B. Offset factor B' is added to the result to produce "B". Control means 28 then asks whether "B" is greater than the interval time I, and if it is, the "on" time is set to I. If not, control means 28 then asks if "B" is less than zero. If so, the "on" time is set to 0 seconds. If the answer to both decision diamonds is no, then the "on" time is set to "B", and the "off" time is set to the interval time I minus "B".

FIG. 2 illustrates a similar logic path for temperature control using the wall temperature differential $D_w$ (the wall setpoint minus the wall sensor reading) in place of the chamber temperature differential.

The gain and offset factors are selected to scale the differential D into an "on" time for the heaters. The setpoint temperature, gain and offset factors may all vary according to the particular sterilizer chamber, the type of sterilization cycle, and other performance considerations. For a steam cycle, the chamber setpoint (or the wall setpoint during warm-up) must be at least 121° C., but may be as high as about 160° to 170° C. Both the gain factor and the offset factor are empirically selected. For a chemical cycle, the wall setpoint is selected to be appropriate for the particular type of chemical. Chemicals which may be used include formaldehyde/alcohol vapor, hydrogen peroxide vapor, and ethylene oxide gas.

In a working embodiment of the invention, a chamber of total mass about 58 kilograms of stainless steel has two 40 watt heat elements on the top, two 75 watt heat elements on the door, two 50 watt heat elements on the back, two 90 watt elements on each of two sides, and two 215 watt heat elements on the bottom forming a first heat zone. A second heat zone comprises two 600 watt heaters also attached to the chamber bottom. In this working embodiment, the setpoint for the chamber temperature of a steam cycle is 154° C., the gain factor is 0.20, and the offset is zero. The "on" time is then given in units of tenths of seconds, e.g., if the calculation yields a value of 100, the "on" time is ten seconds. The gain factor for the wall temperature branch is zero. Accordingly, the "on" time for the steam cycle is based on the chamber temperature differential.

For the same working model, the wall setpoint for a chemical cycle or for a warm-up cycle is 138° C., the gain factor is 0.8, and the offset is zero.

Figure 4:
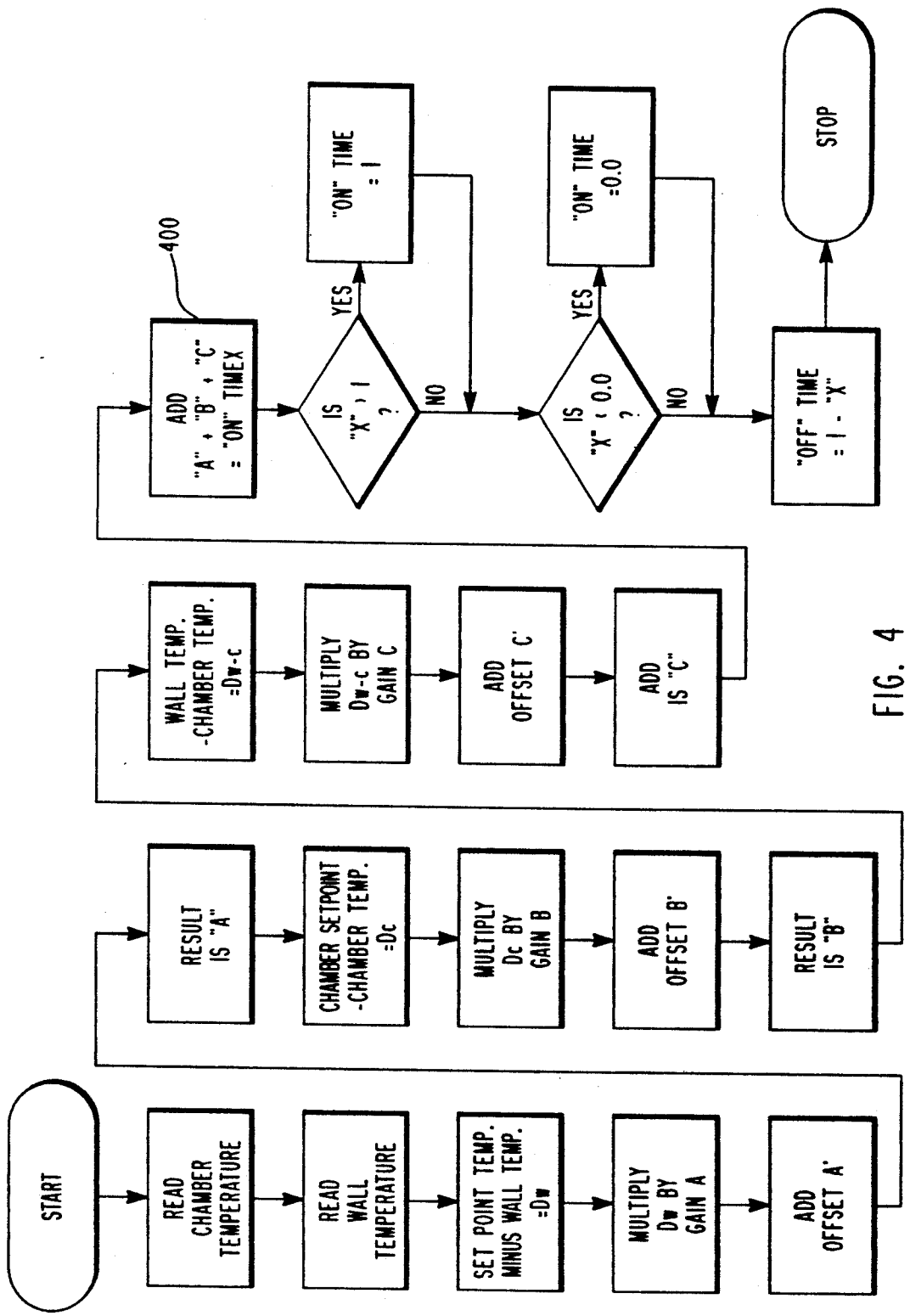
FIG. 4 is a logic flow diagram of an alternate embodiment of the control means of the invention.

Control means 28 selects the logic path of either FIG. 2 or FIG. 3 depending upon the operating mode. Alternatively, control means 28 may use a single logic path as shown in FIG. 4. In this embodiment, when only one temperature differential is being applied, the gain factor for the other differentials is set to zero. For example, in a steam cycle to be regulated in proportion only to the chamber temperature differential $D_c$, control means 28 would set gain factors A and C to zero. The sum in block 400 would then be 0+"B"+0="B", the same as in FIG. 3. Similarly, for a warm-up or chemical phase, gain factors B and C would be set to zero.

In the embodiment of FIG. 4, control means 28 is further operable to adjust the heat input during a chemical cycle to be proportional to the difference between the wall temperature and the chamber temperature (hereinafter referred to as the wall-chamber differential $D_{w-c}$). Although the wall temperature provides the most accurate basis for controlling the temperature of a chemical cycle, it is still important that the chamber temperature be accurate. Thus, for a preferred embodiment to control chemical cycles, control means 28 sets only gain factor B to zero. The "on" time X then includes both the wall temperature differential $D_w$ and the wall-chamber temperature differential $D_{w-c}$.

The length of the operating cycle is chosen to give an adequate response time. The response time is the time required for changes in the operating cycle to result in changes in the wall or chamber temperatures. The response time depends generally on the wattage of the heaters and the rates of heat transfer to and heat loss from the chamber, which in turn depend on chamber size and the construction of the walls. In the working model described previously herein, operating cycle periods of 10 to 20 seconds are found to be appropriate.

The disclosed proportional heat control can be used with steam sterilization cycles and chemical sterilization cycles. Chemical sterilants may include alcohol/formaldehyde mixtures, and ethylene oxide in combination with fluorocarbons or carbon dioxide.

The proportional heat control means is described with reference to a particular embodiment for an electrically-heated, unplumbed single-walled sterilizing chamber. (A plumbed sterilizer is defined as one requiring an external steam source; an unplumbed sterilizer has a reservoir of water which is heated by the sterilizer itself to produce steam.) However, the apparatus and method can also be applied to control temperature in a plumbed, jacketed sterilizer chamber where the walls of the chamber are heated by means of steam injected into the jacket.

Figure 5:
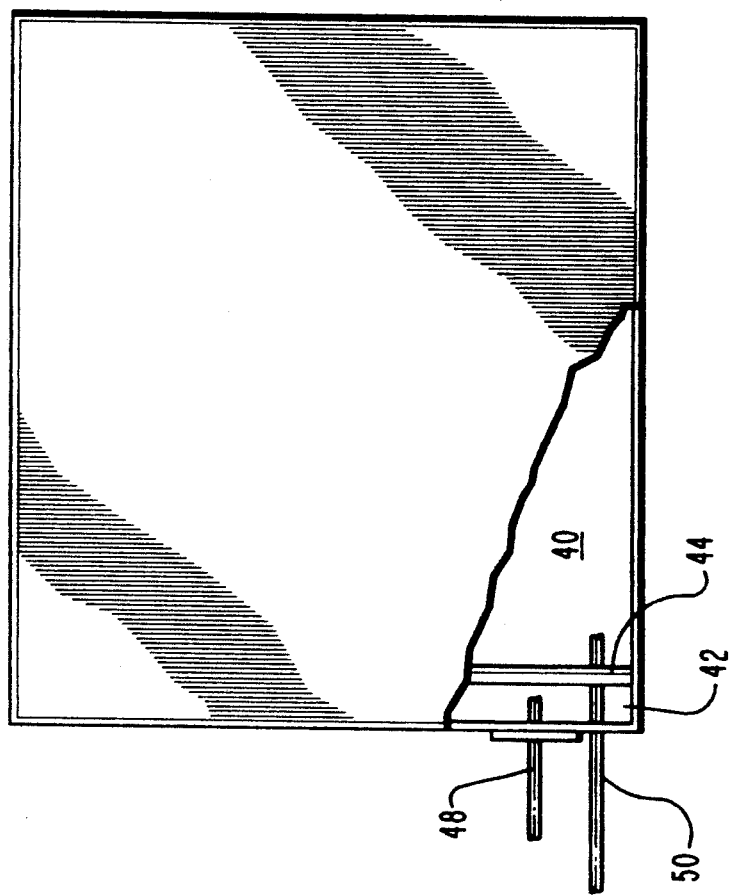
FIG. 5 is a diagram similar to FIG. 1 illustrating an alternative embodiment.

FIG. 5 illustrates an alternative sterilizing apparatus in which the sterilizing chamber 40 includes a jacket chamber 42 surrounding the sterilizer chamber walls 44. The heat source for this embodiment includes steam lines 48 and 50 operable to inject steam into either the chamber 40 or the jacket chamber 42.

While the invention is described with reference to particular embodiments, it will be recognized that various modifications and substitutions may be made without departing from the concept and essence of the invention. The claims themselves define the scope of that which applicants regard as the invention.

What is claimed is:

1. A sterilizing apparatus providing proportional heat control, comprising:
   a sterilizing chamber enclosed by walls;
   heat source means operably disposed for heating said walls, and functional to provide heat input at a constant rate to said walls and thereby to said chamber;
   wall temperature sensing means disposed on said walls for sensing the temperature thereof;
   chamber temperature sensing means disposed within said chamber for sensing the temperature therein; and
   control means operably connected with said heat source means for controlling said heat source means, communicatively connected to said wall and chamber temperature sensing means, and constructed to control said heat source means to provide heat input in proportion to a temperature differential which comprises the difference between a selected setpoint temperature and a sensed temperature sensed by one of said wall and chamber sensing means.

2. The sterilizing apparatus of claim 1, wherein said control means is further constructed to control said heat source means to provide heat input in a series of periods having a fixed interval and to vary the said heat source means being turned on for a fractional portion of each interval, and wherein said control means is constructed to determine the fractional portion according to the temperature differential.

3. The sterilizing apparatus of claim 1, wherein said control means is further constructed to control said heat source means during a steam cycle to provide heat input proportional to a temperature differential which is a chamber temperature differential comprising a chamber setpoint temperature minus an actual chamber temperature sensed by said chamber temperature sensing means.

4. The apparatus of claim 3, wherein said control means is further constructed to control said heat source means during a chemical cycle according to a wall temperature differential which comprises a wall setpoint temperature minus an actual wall temperature sensed by said wall temperature sensing means.

5. The apparatus of claim 4, wherein said control means is further constructed to control said heat source means during a warm-up phase of either a steam sterilization cycle or a chemical sterilization cycle to provide heat input in proportion to a wall temperature differential which comprises a wall setpoint temperature minus an actual wall temperature sensed by said wall temperature sensing means.

6. The sterilizing apparatus of claim 4, wherein said control means is further constructed to control said heat source means during a chemical cycle to achieve the setpoint temperature in said walls.

7. The sterilizing apparatus of claim 6, wherein said control means is further constructed to control said heat source means during a steam cycle to achieve the setpoint temperature in said chamber.

8. The sterilizing apparatus of claim 7, wherein said heat source means comprises electric heaters mounted exteriorly to said walls.

9. The sterilizing apparatus of claim 7, wherein said sterilizing chamber further includes a jacket chamber surrounding said walls, and said heat source means is a steam source arranged to inject steam into either said chamber or said jacket chamber.

10. In an apparatus for sterilizing medical items and having a sterilization chamber with heating means for heating the chamber walls and thereby the chamber interior, a wall temperature sensor mounted on the outside of one of the walls, a chamber temperature probe disposed within the chamber interior, and control means connected to the wall temperature sensor and chamber temperature probe and to the heating means for controlling the heat input and thereby the temperature of the chamber during sterilization cycles in response to temperatures sensed by said wall temperature sensor and/or chamber temperature probe the improvement comprising said control means being constructed to adjust said heating means to provide heat input in response to a temperature differential which comprises a setpoint temperature minus a sensed temperature sensed by one of said wall temperature sensor and said chamber temperature probe.

11. An improvement according to claim 10, wherein said control means is further constructed to control said heating means during a steam cycle to provide heat input to achieve a setpoint temperature in said chamber interior.

12. An improvement according to claim 11, wherein said control means is further constructed to control said heating means during a steam cycle to provide heat input to achieve a setpoint temperature in said chamber walls.

13. An improvement according to claim 12, wherein said control means is further constructed to control said heating means during a warm-up phase prior to either steam or chemical cycles to provide heat input to achieve the setpoint temperature in said chamber walls.

14. An improvement according to claim 13, wherein said heating means functions according to time intervals of preset equal lengths, said heating means being turned on for a fractional portion of each interval, and wherein said control means is constructed and arranged to determine the fractional portion according to the temperature differential.

15. A method of controlling heating of a sterilizer chamber including a chamber with walls, heating means arranged for heating said walls and thereby said chamber, wall temperature sensing means disposed for sensing the temperature of the walls, chamber temperature sensing means disposed for sensing the temperature within said chamber, and control means connected to receive sensed temperatures from the wall and chamber temperature sensing means and to control the heating means to provide heat input to the walls to achieve and maintain a desired setpoint temperature of the walls or within the chamber, comprising the steps of:

taking a temperature reading from one of the wall or chamber temperatures sensing means;

subtraction the temperature reading from the desired setpoint temperature to produce a temperature differential;

determining a heat input value proportional to the temperature differential; and regulating the heating means to generate heat in the amount of the heat input value to the chamber walls.

16. The method of claim 15, further including the step of selecting a fixed operating interval, wherein the heat input value is a selected fraction of the fixed operating interval, and said step of regulating the heating means comprises turning the heating means on for the selected fraction and off for the remainder of the fixed operating interval.

* * * * *